United States Patent [19]
O'Donnell, Jr.

[11] Patent Number: 6,096,029
[45] Date of Patent: *Aug. 1, 2000

[54] LASER METHOD FOR SUBSURFACE CUTANEOUS TREATMENT

[75] Inventor: Francis E. O'Donnell, Jr., St. Louis, Mo.

[73] Assignee: Laser Skin Toner, Inc.

[ * ] Notice: This patent issued on a continued prosecution application filed under 37 CFR 1.53(d), and is subject to the twenty year patent term provisions of 35 U.S.C. 154(a)(2).

[21] Appl. No.: 08/804,931

[22] Filed: Feb. 24, 1997

Related U.S. Application Data

[60] Provisional application No. 60/023,252, Aug. 12, 1996.

[51] Int. Cl.⁷ .................................................. A61B 17/36
[52] U.S. Cl. ...................................... 606/9; 606/3
[58] Field of Search .................. 607/96, 98–104, 607/88, 89; 128/897, 898; 606/4, 2, 5, 3, 9, 13

[56] References Cited

U.S. PATENT DOCUMENTS

| | | | |
|---|---|---|---|
| 4,976,709 | 12/1990 | Sand | 606/5 |
| 5,057,104 | 10/1991 | Chess | 606/9 |
| 5,282,797 | 2/1994 | Chess | 606/9 |
| 5,507,790 | 4/1996 | Weiss | 607/100 |
| 5,611,795 | 3/1997 | Slatkine et al. | 606/9 |
| 5,660,836 | 8/1997 | Knowlton | 607/96 |

*Primary Examiner*—Lee Cohen
*Assistant Examiner*—Bryan K. Yarnell
*Attorney, Agent, or Firm*—Seidel, Ganda, Lavorgna & Monaco, PC

[57] ABSTRACT

A laser method for selective photocoagulation of subsurface skin (dermis) for the purpose of increasing skin tone, reducing wrinkles, removing hair, removing tattoos or treating varicose veins without damaging the skin surface (epidermis). A diffuser lens in the laser apparatus is employed to focus the laser energy to the dermis. The laser apparatus includes a highly transmissive contact tip and cooling means to reduce heat build-up in the contact tip, as monitored by a thermocouple mechanism. The present invention can be used alone or in conjunction with superficial laser resurfacing or chemical peels to increase skin tone.

7 Claims, 4 Drawing Sheets

Trichrome stain of breast skin after treatment with 1064 nm laser. The bar respresents 500 microns on the top picutre and 60 microns on the bottom. The arrows show the approximate edges to the zones of thermal damage.

LASER METHOD FOR SUBSURFACE CUTANEOUS TREATMENT

CROSS REFERENCE TO RELATED APPLICATIONS

This application claims priority to provisional application Ser. No. 60/023,252, filed Aug. 12, 1996.

STATEMENT REGARDING FEDERALLY SPONSORED RESEARCH OR DEVELOPMENT

Not applicable.

BACKGROUND OF THE INVENTION

The present invention relates to an apparatus and method of laser treatment of subsurface cutaneous tissue for the purpose of effecting a tightening of the skin and reducing wrinkles without significantly altering the epidermis.

Pulsed $CO_2$ lasers, erbium lasers, holmium lasers, and other infrared lasers are being used clinically to remove the epidermis and superficial reticular dermis for the purpose of laser resurfacing. Besides removing the superficial layers, there is often a significant contraction of the skin associated with these laser resurfacing technologies. This skin tightening is due to sufficient, but not excessive dermal collagen heating by the laser, and it is as important to patient satisfaction as the more youthful epidermis (skin surface) appearance achieved by laser resurfacing.

Unfortunately, in order to achieve this skin tightening, it has been necessary to remove the epidermis with the laser. This results in a raw skin surface that is unsightly, and that requires extensive wound care for weeks. Attempts to reduce these unwanted morbidities by using lasers for resurfacing that do not have as much collateral thermal damage result in inadequate tightening of the skin. For example, a pulsed $CO_2$ laser of 100 microseconds or so duration (e.g., Tru-Pulse, Tissue Technologies, Inc., Albuquerque, N. Mex.) cause less postoperative erythema, swelling, and discomfort than pulsed $CO_2$ laser of one millisecond pulse duration (e.g., Nova-Pulse, Luxar, Inc., Redmond, Wash.), but they do not tighten the skin as much as the longer-pulsed $CO_2$ lasers.

Wrinkle removal by pulsed infrared lasers during resurfacing is a result of removal of the epidermis and reticular dermis at the same time. Skin tightening requires deeper thermal effects than wrinkle removal. Thus attempts to reduce postoperative erythema, pain and swelling by doing a more superficial resurfacing do not result in adequate skin tightening.

Prior art (e.g.,U.S. Pat. Nos. 4,976,709 and 5,484,432) attempts to selectively treat subsurface collagen without damaging the surface have been primarily related to corneal treatment (laser thermal keratoplasty) for corrections of refractive errors using infrared wavelength greater than 1.8 micron. Moreover, treatment parameters identified were selected so as to avoid a cicatrix which might impair the transparency of the cornea. For example, preferred embodiments included small (<2 mm in diameter) spot size, short pulse duration (0.1 sec), a fluence up to $100J/CM^2$ and non-contact delivery means.

Contact handpieces and non-contact delivery means for laser treatment of the eye have included designs which allow for surface-sparing of the ocular tissues, but delivery of a photocoagulation to internal tissues such as the ciliary body in glaucoma management. In U.S. Pat. No. 5,514,125, for example, a contact handpiece for delivery of laser energy to the ciliary processes in glaucoma is described. It features a fiberoptic distal member separated from a focusing lens at the contact tip for the purpose of reducing scatter of the laser energy.

Controlled subsurface laser energy also can be used to remove hair, tattoos and varicose veins. A contact subsurface laser energy delivery system that can target the follicle and not damage the sebaceous glands and sweat glands and the skin between the hairs would be advantageous. Further as system for removing tattoos and treating varicose veins by the subsurface application of laser energy is desirable.

SUMMARY OF THE INVENTION

It is an object of the present invention to effect a significant tightening (contracture) of the skin without appreciable damage to the epidermis.

Accordingly, it is another object of the present invention to increase skin tone by effecting a contracture of the skin without affecting the overlying epidermis.

It is a further object of the present invention to reduce wrinkle formation by treating the underlying dermis without damage to the epidermis.

It is an object of the present invention to use an effective laser modality for skin tightening and wrinkle elimination which can be done without causing temporary disability to the patient.

It is a further object of the present invention to allow for repeated laser treatments as often as necessary to maintain skin tone and surface smoothness.

It is another object of the invention to provide a handpiece for contact delivery of infrared laser energy using treatment parameters determined to accomplish the foregoing objects of the invention.

It is another object of the invention to provide a variable focus handpiece for contact delivery of laser energy wherein the variable depth of laser treatment is achieved by varying the distance between the focusing lens and the tip of the fiberoptic bundle.

It is another object of the invention to provide a method and apparatus for the delivery of subsurface laser energy to remove unwanted hair.

Still another object of the invention is to provide a method and apparatus for for the subsurface delivery of laser energy to remove tattoos.

Yet another object of the invention is to provide a method and apparatus for the subsurface delivery of laser energy to treat varicose veins.

In accordance with the invention, briefly stated, the present invention provides for photocoagulation of the dermis that spares the epidermis. For this domain of wavelengths, for example, the exact combination of parameters selected for power setting and spot size must deliver more than $100J/CM^2$ of laser energy fluence. With respect to pulse length, the pulse duration must be in excess of the thermal relaxation time of dermis (i.e., greater than 60 milliseconds) unless the laser delivers a train of short pulses ("micropulses") wherein the duty cycle selected results in an interval between pulses of less than approximately 60 milliseconds. For a given fluence, the pulse duration selected must be adequate to raise the temperature of the dermis to approximately 70° C. yet spare the epidermis.

DESCRIPTION OF THE PREFERRED EMBODIMENT

Figure 1:
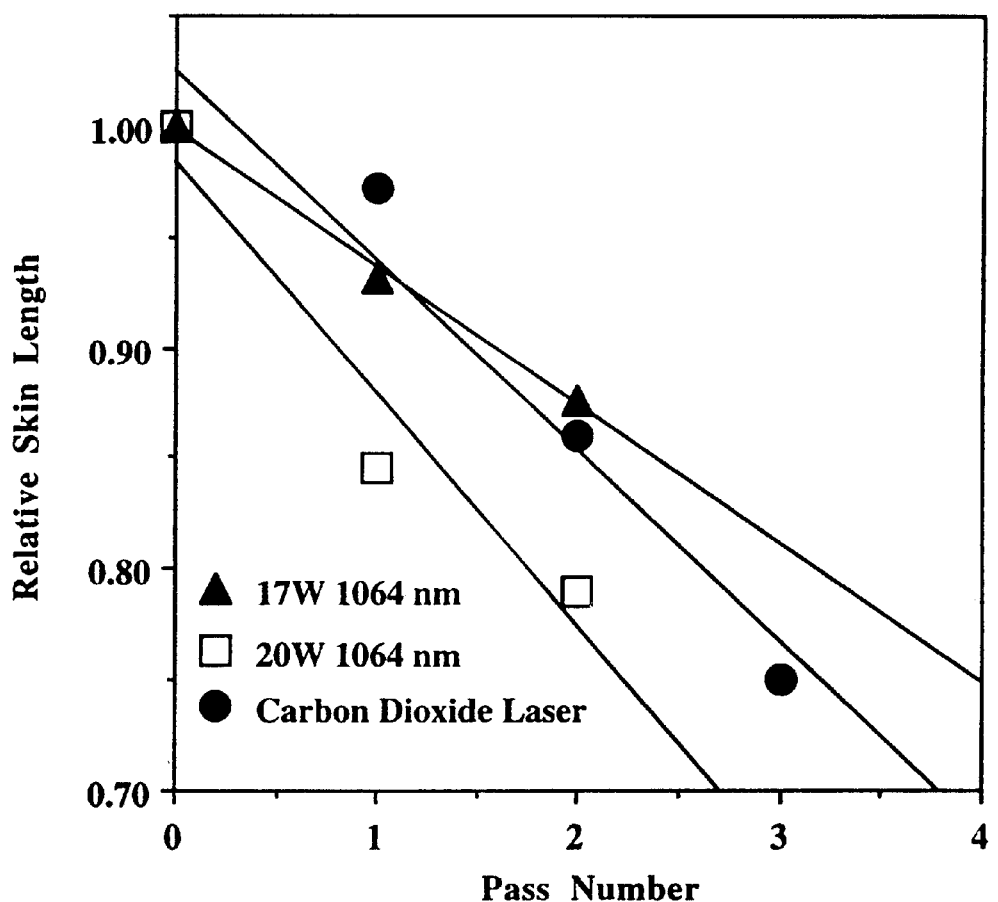
FIG. 1 is a graph illustrating the relative amount of skin shrinkage based upon the laser employed in the method of the present invention.

The method of the present invention comprises the application of laser energy to the skin to effect better skin tone. The method, as described in greater detail hereinafter, sufficiently photocoagulates the dermis but avoids damage to the epidermis to increase skin tone and reduce wrinkles. The method employees a laser handpiece designed to allow for subsurface photocoagulation of the dermis without attendant visible damage to the overlying epidermis. Further, the method of the present invention includes a short-pulsed or superficial laser resurfacing.

In one preferred embodiment of the present invention, a contact handpiece with a hemispheric or convex transmissive tip is used to deliver approximately 10-watt to 250-watt pulses of 0.1 to 0.5 second duration of wavelengths of 800 nanometers to 1.79 microns and a spot size of 2 millimeters to 5 millimeters in diameter to yield a fluence of more than $100J/CM^2$. A typical handpiece for the method of the present invention is shown schematically in FIG. 4 and will be described in greater detail below.

A wavelength in the range of 800 nanometers to 1.79 microns is selected because this part of the spectrum is poorly absorbed by melanin in the epidermis and by hemoglobin in the dermal blood vessels. The laser energy is transmitted through the epidermis and effects shrinkage of the underlying dermis. Therefore, the risk of pigmentary disturbance and ecchymosis is reduced. Moreover, this part of the spectrum is only modestly absorbed by water making deeper penetration into the dermis possible than longer infrared wavelengths.

A pulse duration of 0.1 second to 0.5 second allows for photocoagulation effects in this range of the spectrum within the dermis by exceeding the thermal relaxation time of the dermis, estimated to be about 60 milliseconds (0.060 second). By avoiding excessively long pulse durations, the chance of thermal conduction to overlying epidermis is reduced. Obviously, deeper dermal photocoagulation allows for longer pulse duration at the same power setting. A power setting of 10 watts to 250 watts for pulse durations of 0.1 second to 0.5 second duration provides a sufficiently adequate fluence (greater than $100J/CM^2$) for spot sizes of 2 millimeters to 5 millimeters in diameter to effect a photocoagulation of the dermis. The pulse duration of 0.1 second to 0.5 second is effective for the intended purpose by does not burn the skin surface. By delivering sufficient energy to raise the dermal temperature to approximately 70° centigrade, a contracture of the dermis occurs.

It should be obvious that variations on these parameters are possible depending upon wavelength, power settings, pulse duration, and spot size selected.

The size of the contact tip is preferably 2 to 5 mm in diameter, but variations on the diameter are possible by adjusting the optics within the handpiece or by adjusting the shape and the curvature of the tip (asphericity) to appropriately focus the depth of the photocoagulation in the dermis. Moreover, variations in tip diameter necessitate the appropriate adjustment of power to achieve adequate fluence and adjustment of pulse duration to deliver enough energy to raise the temperature of the dermis without damaging the epidermis.

The contact handpiece is highly transmissive to the selected wavelength in order to avoid heating of the tip, which would damage the epidermis. The tip material must be highly transmissive for the selected wavelength. Examples of suitable materials include silicone, fiberglass, pyrex glass, quartz, sapphire, diamond, polymethylmethacrylate, acrylic, and polycarbonate. The tip and the skin must be kept dry and clean during the treatment for the same reason. Various optical means can be used to defocus the laser energy at the tip. A convex or hemispheric contour to the contact tip further reduces the risk of focusing the laser energy too superficially. Incorporation of diffuser optics in the handpiece can reduce the risk of focusing the laser energy on the skin surface. The tip design may include a mechanism for cooling, such as air, gas, or liquid flow. The coolant may be refrigerated in order to further reduce the temperature at the point of contact with the skin.

In another preferred embodiment, monitoring the temperature of the contact tip can provide a sensing means to avoid thermal injury to the surface (epidermis). A thermocouple at the tip can be used. Alternatively, the temperature differential between coolant ingress and coolant egress from the tip can be used to detect unwanted temperature increases at the tip.

FIG. 1 demonstrates the linear relationship between contiguous laser spot placements (i.e., number of passes) and the amount of skin contraction using a wavelength of 1.06 microns (neodymium Nd:YAG), 0.4 second pulse duration, and a power setting of 17 watts with a hemispheric quartz tip of approximately 2.2 millimeters in diameter (fluence at the tip of approximately $180J/CM^2$) with air cooling. For comparison, the tissue contraction induced by a pulsed $CO_2$ resurfacing laser (Nova-Pulse, Luxar, Inc., Redmond, Wash.) is plotted as well. The present invention is as effective as the resurfacing laser for skin contraction, but the present invention causes no damage to the skin surface (epidermis).

Figure 2:
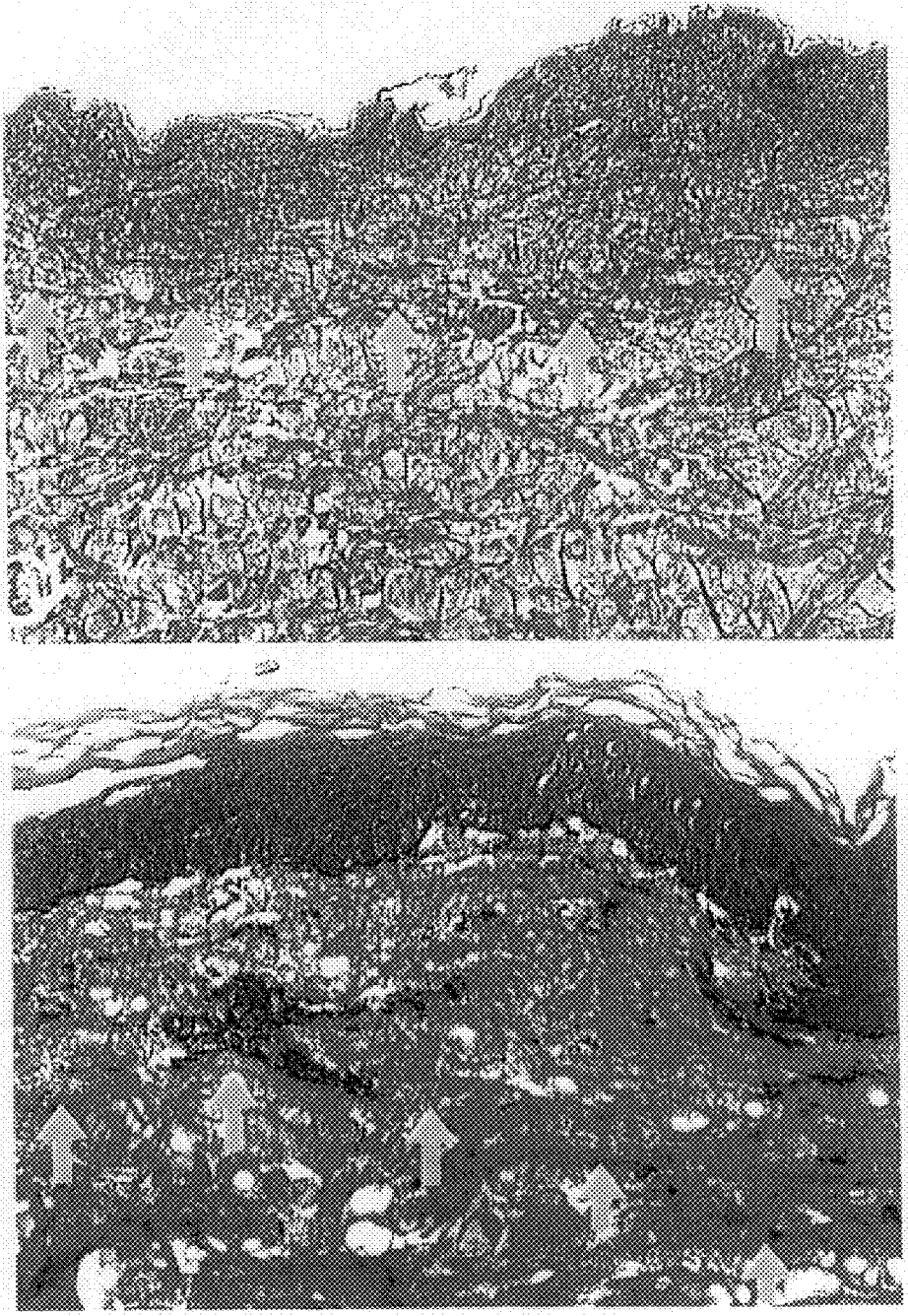
FIG. 2 is a photomicrogram illustrating breast skin treated with a 1064 nm laser.

The lack of epidermal damage and the zone of photocoagulative effect in the upper dermis of the present invention is demonstrated in FIG. 2.

Figure 3:
FIG. 3 is a photomicrogram illustrating breast skin treated with a 1064 nm laser.

In another preferred embodiment, firm pressure of the contact handpiece upon the skin during application of the energy deepens the depth of the photocoagulation well below the epidermal surface (FIG. 3) providing additional protection for the epidermis.

In another preferred embodiment, the placement of a diffuser lens within the handpiece between the fiberoptic element and the contact tip causes an adjustable displacement of the focal point of the laser (FIG. 4) so that the epidermis is spared, and the clinical effect can be modulated by depth of photocoagulation.

In another preferred embodiment of the present invention, the subsurface laser treatment is performed either before or after a superficial laser resurfacing or a short-pulsed infrared laser treatment. Thus the present invention makes it possible to use superficial laser resurfacing with less thermal damage and thereby allows for faster recovery.

In another preferred embodiment of the present invention, the subsurface laser treatment is performed either before or after a chemical peel. Improvements in chemical peels, such as glycolics, have made it possible to resurface the skin without a laser. Unfortunately, chemical peels do not provide sufficient tightening of the skin. The present invention is used before or after the peel to provide enhanced skin tone (skin contraction) in place of a deep laser resurfacing procedure.

Figure 4:
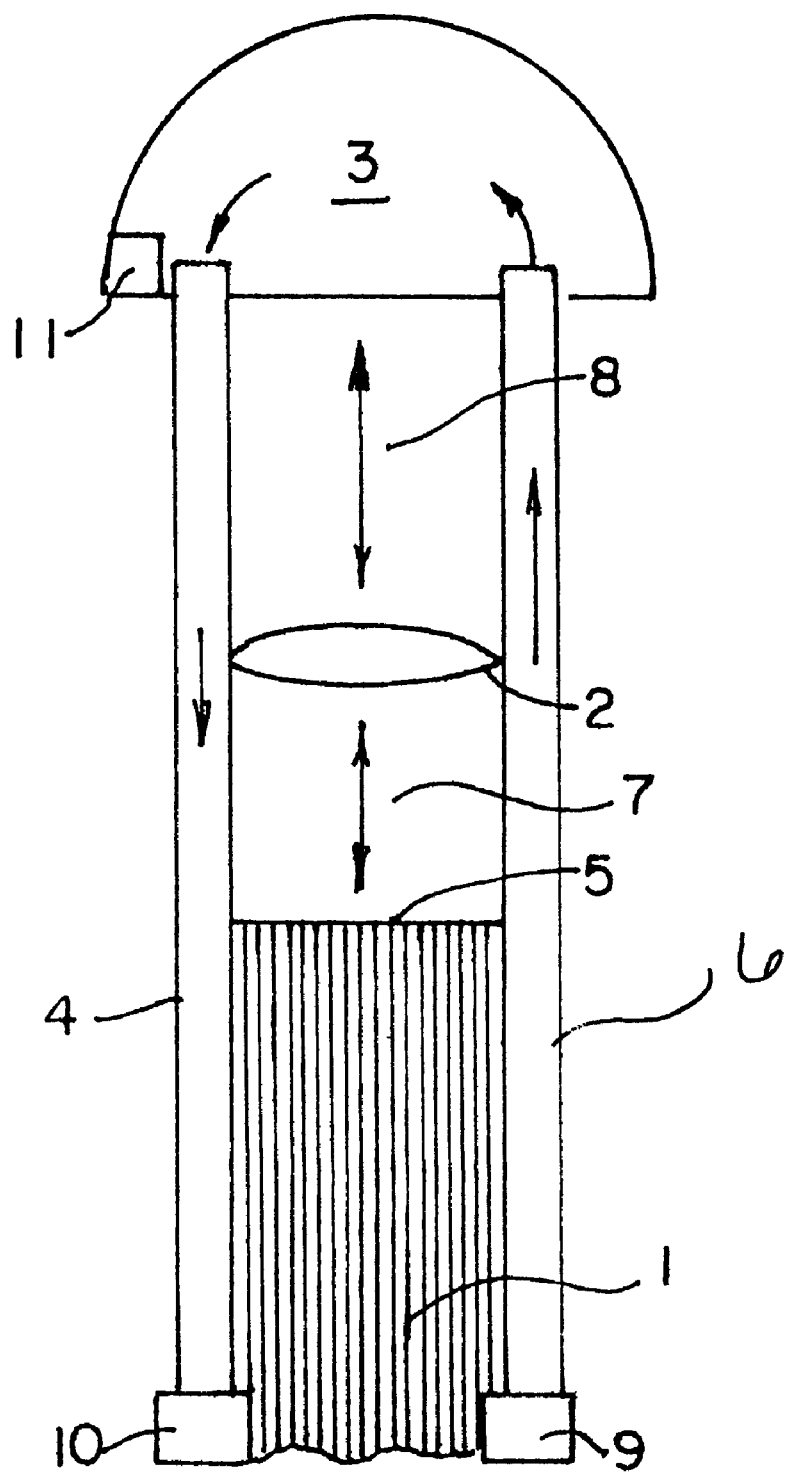
FIG. 4 is a schematic of a laser handpiece used in the method of the present invention.

FIG. 4 illustrates a preferred embodiment of the laser handpiece employed in the method. The handpiece includes a fiberoptic bundle 1, a diffuser lens and a transmissive tip 3 which is the upper terminal end of a non-transmissive sleeve 4. The tip 3 which is cooled by air, gas (e.g., $CO_2$ or $N_2$) which may flow into the tip through an outer chamber 6 and return via a return path 5. Transmissive tip 3 may be constructed of materials such as fiberglass, quartz, sapphire, diamond, polymethylmethacrylate (PMMA), polycarbonate, silicone, and pyrex glass. Transmissive tip 3 may be concave, plano (flat), or convex (hemispheric). Tip 3, however, is highly transmissive to avoid heat build-up at the tip. The diffuser lens 2 can be positioned during manufacturing or variably by the operator. The diffuser lens 2 can be changed in position, as shown by arrows 7 and 8, to determine the focal point of laser energy transmitted by tip 3 Diffuser lens 2 may be a convergent lens in which case the focal point is proximal to the contact tip or a divergent lens. The diffuser lens 2 can defocus the laser energy off the skin surface and deliver the laser energy to the dermis. Thermocouples 9 and 10 can be used to detect temperature increases at the tip 3 which could cause thermal damage to the epidermis. Alternatively, a thermocouple 11 in the tip can be used to directly sense the temperature at the tip.

To remove unwanted hair, the previously described contact handpiece is placed over the hair orifice. The handpiece can be set at an angle so as to focus the laser emission along the path of the hair to the subepidermal hair bulb. The diffuser lens 2 can be used to tightly focus the laser emission (for example, to an area less than 500 micrometers in diameter) suprathreshold fluence at the target is achieved regardless of growth phase, pigment content or vascularization.

The method and apparatus of the present invention also can be used to remove tattoos from the dermis by controlled or focused application of laser energy. Moreover, a surgeon also can use the method and device to treat varicose veins.

It is apparant from the foregoing that various changes and modifications can be made in the method and apparatus the present invention without departing from the scope of the appended claims. Therefore, the foregoing description and accompanying drawings are intended to be illustrative only and should not be construed in a limiting sense.

What is claimed:

1. Method of increasing skin tone and reducing wrinkles, comprising the steps of
   a. contacting a patient's skin with an optically transmissive contact element,
   b. transmitting laser energy at wavelengths from about 800 nanometers to about 1.79 microns from a laser energy source to the patient's skin through the contact element,
   c. focusing the laser energy to a location below the epidermis of the patient's skin to achieve a spot size of between about 2 mm and about 5 mm in diameter and an energy fluence of not less than 100 $J/cm^2$, and
   d. maintaining the contact element in contact with the patient's skin and applying laser energy to the skin for a period of time sufficient to cause photocoagulation of the dermis of the patient's skin while avoiding damage to the epidermis.

2. The method of increasing skin tone and reducing wrinkles according to claim 1, further comprising the step of applying firm pressure of the contact element against the skin.

3. The method of increasing skin tone and reducing wrinkles according to claim 1, further comprising the step of applying a variable pressure of the contact element against the skin to vary the depth of photocoagulation of the dermis.

4. The method of increasing skin tone and reducing wrinkles according to claim 1, further comprising the step of cooling at least the portion of the contact element in contact with the patient's skin.

5. The method of increasing skin tone and reducing wrinkles according to claim 1, further comprising adjusting the laser energy of the laser energy source for obtaining a desired energy fluence.

6. The method of increasing skin tone and reducing wrinkles according to claim 1, further comprising pulsing the laser energy of the laser energy source.

7. The method of increasing skin tone and reducing wrinkles according to claim 6, wherein the pulse duration of the laser energy of the laser energy source is between about 0.1 seconds and about 0.5 seconds.

\* \* \* \* \*